(12) United States Patent
Hajianpour

(10) Patent No.: US 9,132,018 B1
(45) Date of Patent: Sep. 15, 2015

(54) TOTAL ANKLE REPLACEMENT

(71) Applicant: Mohammed A. Hajianpour, Fort Lauderdale, FL (US)

(72) Inventor: Mohammed A. Hajianpour, Fort Lauderdale, FL (US)

(*) Notice: Subject to any disclaimer, the term of this patent is extended or adjusted under 35 U.S.C. 154(b) by 0 days.

(21) Appl. No.: 13/950,474

(22) Filed: Aug. 27, 2013

(51) Int. Cl.
*A61F 2/42* (2006.01)

(52) U.S. Cl.
CPC ....... *A61F 2/4202* (2013.01); *A61F 2002/4205* (2013.01); *A61F 2002/4207* (2013.01)

(58) Field of Classification Search
CPC ........... A61F 2/42; A61F 2/4202; A61F 2/30; A61F 2/4606; A61F 2/4607; A61F 2002/4202; A61F 2002/42; A61F 200/4207; A61F 2002/4217; A61F 2002/422; A61F 2002/4223; A61F 2002/4215; A61F 2002/4212; A61B 17/1742; A61B 17/175; A61B 17/1753; A61B 17/7225; A61B 17/562; A61B 17/164; A61B 17/744; A61B 17/72; A61B 17/1717; A61B 17/1725; A61B 17/56; A61B 17/58; A61B 17/6425; A61B 17/6408
USPC ..................................... 623/21.18; 606/92, 62
See application file for complete search history.

(56) References Cited

U.S. PATENT DOCUMENTS

| | | | | |
|---|---|---|---|---|
| 4,069,518 | A * | 1/1978 | Groth et al. ................. | 623/21.18 |
| 4,156,944 | A * | 6/1979 | Schreiber et al. ........... | 623/21.18 |
| 4,450,591 | A * | 5/1984 | Rappaport .................... | 128/898 |
| 4,470,158 | A * | 9/1984 | Pappas et al. ............... | 623/20.21 |
| 5,180,383 | A * | 1/1993 | Haydon ........................ | 606/300 |
| 6,136,032 | A * | 10/2000 | Viladot Perice et al. ... | 623/21.18 |
| 6,579,293 | B1 * | 6/2003 | Chandran ...................... | 606/64 |
| 6,663,669 | B1 * | 12/2003 | Reiley ......................... | 623/21.18 |
| 6,673,116 | B2 * | 1/2004 | Reiley ......................... | 623/21.18 |
| 8,303,667 | B2 * | 11/2012 | Younger ..................... | 623/21.18 |
| RE44,501 | E * | 9/2013 | Janna et al. .................. | 606/62 |
| 2002/0055744 | A1 * | 5/2002 | Reiley .......................... | 606/79 |
| 2003/0097131 | A1 * | 5/2003 | Schon et al. .................. | 606/62 |
| 2004/0122523 | A1 * | 6/2004 | Guzman ..................... | 623/21.18 |
| 2005/0107791 | A1 * | 5/2005 | Manderson ................... | 606/62 |
| 2005/0192673 | A1 * | 9/2005 | Saltzman et al. ........... | 623/21.18 |
| 2005/0229433 | A1 * | 10/2005 | Cachia ........................... | 36/44 |
| 2005/0288792 | A1 * | 12/2005 | Landes et al. .............. | 623/21.18 |
| 2006/0041315 | A1 * | 2/2006 | Katz et al. .................. | 623/21.11 |
| 2006/0229730 | A1 * | 10/2006 | Railey et al. ............... | 623/21.18 |
| 2006/0247787 | A1 * | 11/2006 | Rydell et al. ............... | 623/21.11 |
| 2006/0293676 | A1 * | 12/2006 | Perice et al. ................. | 606/72 |
| 2007/0027547 | A1 * | 2/2007 | Rydell et al. ............... | 623/21.18 |
| 2008/0015587 | A1 * | 1/2008 | Munoz ......................... | 606/62 |
| 2008/0195233 | A1 * | 8/2008 | Ferrari et al. ................ | 623/47 |
| 2008/0208349 | A1 * | 8/2008 | Graser ........................ | 623/21.18 |
| 2008/0221577 | A1 * | 9/2008 | Elghazaly ...................... | 606/64 |
| 2008/0306605 | A1 * | 12/2008 | Hasselman ................ | 623/21.18 |
| 2009/0082818 | A1 * | 3/2009 | Roth ............................ | 606/304 |

(Continued)

*Primary Examiner* — Alvin Stewart

(74) *Attorney, Agent, or Firm* — Ronald V. Davidge

(57) ABSTRACT

An ankle replacement prosthesis includes a tibial component, attached within a cavity formed in the tibia, and a talocalcaneal component, attached within a slot formed within a talocalcaneal compound, previously formed by fusing the talus and the calcaneus. Preferably, the talocalcaneal component includes a neck, to which a head, having a contact surface engaging a contact surface within the tibial component, is adjustably attached. These contact surfaces may both be spherical, with the contact surface of the talocalcaneal component being formed as a ball fitting within a socket formed by the contact surface of the tibial component, or these contact surfaces may include mating feature that limit inversion/eversion rotation of the foot, while providing for dorsal/plantar rotation thereof.

16 Claims, 9 Drawing Sheets

(56) References Cited

U.S. PATENT DOCUMENTS

| | | | |
|---|---|---|---|
| 2009/0082875 A1* | 3/2009 | Long | 623/21.18 |
| 2009/0099571 A1* | 4/2009 | Cresina et al. | 606/96 |
| 2009/0105767 A1* | 4/2009 | Reiley | 606/301 |
| 2009/0149861 A1* | 6/2009 | Brodsky et al. | 606/96 |
| 2009/0177240 A1* | 7/2009 | Perez | 606/86 R |
| 2010/0057216 A1* | 3/2010 | Gannoe et al. | 623/21.18 |
| 2010/0114315 A1* | 5/2010 | Manderson | 623/16.11 |
| 2011/0004212 A1* | 1/2011 | Gall et al. | 606/62 |
| 2011/0054473 A1* | 3/2011 | Brigido | 606/62 |
| 2011/0118792 A1* | 5/2011 | Orsak | 606/301 |
| 2011/0166608 A1* | 7/2011 | Duggal et al. | 606/320 |
| 2011/0282397 A1* | 11/2011 | Richter et al. | 606/304 |
| 2012/0010719 A1* | 1/2012 | Reiley | 623/21.18 |
| 2012/0130370 A1* | 5/2012 | Kinmon | 606/62 |
| 2012/0172936 A1* | 7/2012 | Horrell et al. | 606/319 |
| 2012/0197254 A1* | 8/2012 | Wolfe et al. | 606/62 |
| 2012/0215223 A1* | 8/2012 | Chiodo et al. | 606/70 |
| 2012/0245701 A1* | 9/2012 | Zak et al. | 623/21.18 |
| 2013/0085502 A1* | 4/2013 | Harrold | 606/96 |
| 2013/0116797 A1* | 5/2013 | Coulange et al. | 623/21.18 |
| 2013/0325006 A1* | 12/2013 | Michelinie et al. | 606/62 |
| 2013/0325076 A1* | 12/2013 | Palmer et al. | 606/318 |
| 2013/0331947 A1* | 12/2013 | Surma et al. | 623/21.12 |
| 2014/0088717 A1* | 3/2014 | Boyden et al. | 623/19.11 |
| 2014/0107798 A1* | 4/2014 | Jeng et al. | 623/21.18 |
| 2014/0114313 A1* | 4/2014 | Early et al. | 606/64 |
| 2014/0142575 A1* | 5/2014 | Biedermann et al. | 606/62 |
| 2014/0180426 A1* | 6/2014 | Lian | 623/20.15 |
| 2014/0228845 A1* | 8/2014 | Gorsline et al. | 606/62 |
| 2015/0045902 A1* | 2/2015 | Perler | 623/21.18 |
| 2015/0057665 A1* | 2/2015 | Neal et al. | 606/87 |

* cited by examiner

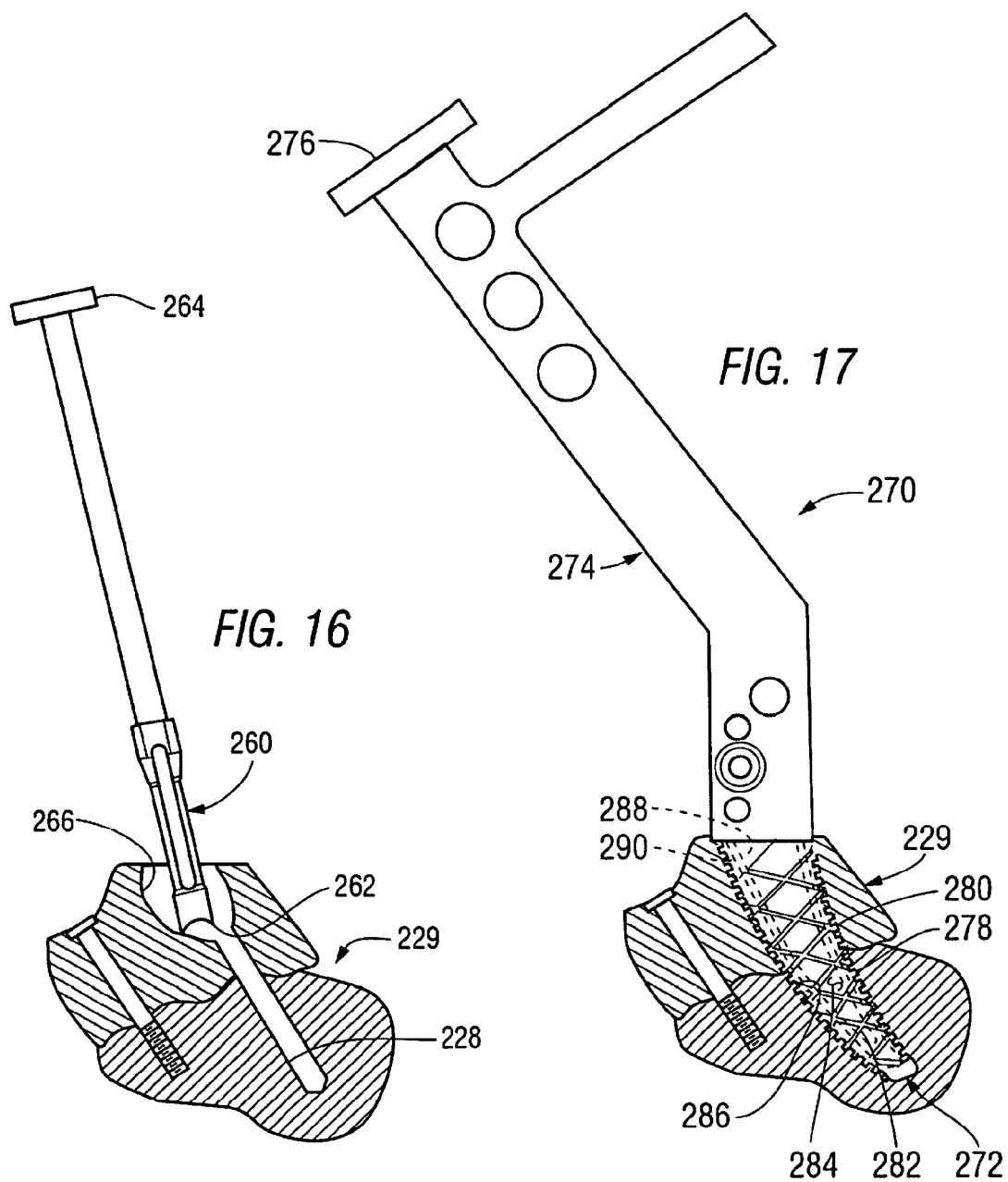

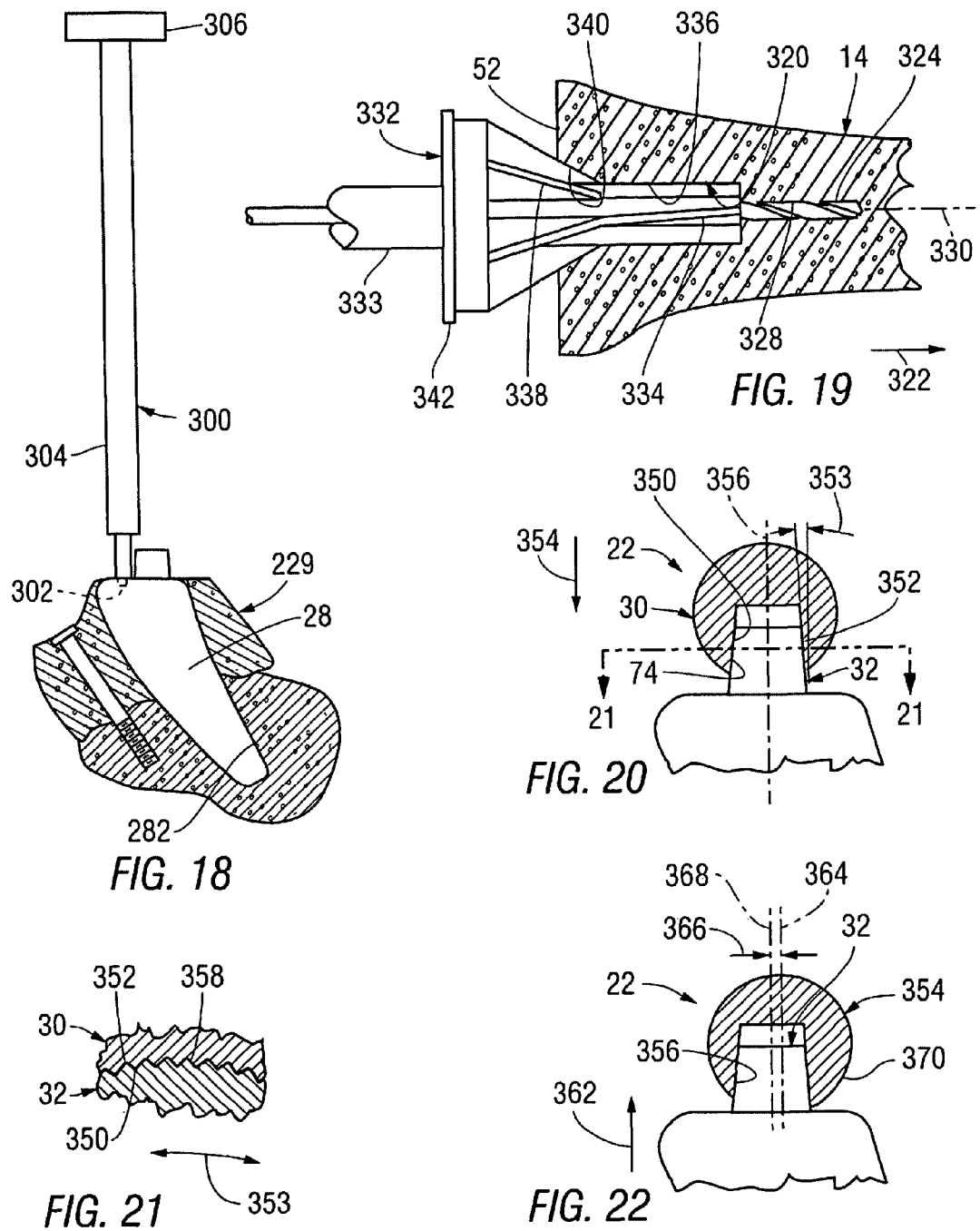

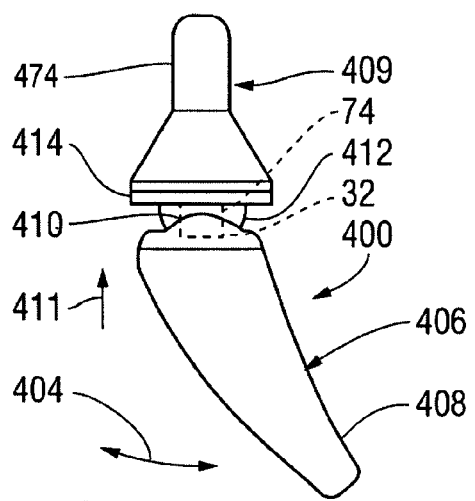

TOTAL ANKLE REPLACEMENT

RELATED APPLICATIONS

Not Applicable

FEDERALLY SPONSORED RESEARCH OR DEVELOPMENT

Not Applicable

BACKGROUND OF THE INVENTION

1. Field of the Invention

This invention relates to a method and a prosthesis for total ankle replacement.

2. Summary of the Background Information

A surgeon begins a conventional ankle replacement process by making an incision in front of the ankle. Then, portions of the tibia and talus forming the damaged joint surfaces are removed through the incision and the surfaces of the tibia and talus are shaped to accept and hold the mating surfaces of the prosthesis, which is then inserted through the incision for attachment. The distal end of the fibula may be fused to the tibia with a bone graft so that compression forces resulting from the subsequent application of weight to the prosthesis will be carried by the fibula as well as by the tibia. When the surgeon has determined that the prosthesis has been properly installed, the incision is closed.

A conventional ankle prosthesis includes a tibial component and a talocalcaneal component, which have bearing surfaces adjacent to one another that are nearly congruent and cylindrically curved, in a longitudinal direction, parallel to the length of the foot, while the wear surfaces are straight in a lateral direction, across the width of the foot. Lateral movement between the tibial and talus components is limited by flanges extending from one of the components past the wear surface of the other component. Axial rotation may be provided through the use of plates turning against one another. While flexure within the prosthesis in the plantar and dorsal directions is permitted by the curvature of the bearing surfaces, flexure in the inversion and eversion directions is prevented by the shape of the wear surfaces, which are straight in the lateral direction.

Conventional ankle replacement provides the patient with foot movement allowing a nearly normal gait, following recovery. While the patient can walk and perform low-impact exercises, he is cautioned against performing high-impact exercises, such as step aerobics and the use of an inclined treadmill or stairstep machine. The effective life of the prosthesis is dependent on how it is used after recovery, with problems occurring particularly due to loosening of the components from the bone surfaces to which they are attached, requiring surgical correction, possibly with ankle fusion. While such problems are associated with limitations in the bone stock available for the attachment of the prosthetic components, it is known that weakening of bone within the talus results in part from the fact that a conventional talar implant produces high stresses in an annular area of the talus while shielding an area within the annular area from stresses. It is further known that a high percentage of patients with post traumatic or osteoarthritic degradation of the ankle joint also have subtalar advanced disease and related pain, and that subtalar fusion in the presence of a conventional ankle replacement prosthesis increases stress levels, expediting failure. Thus, what is needed are improvements in attachment of the prosthetic components to bone and provisions for increasing the allowed movement between the prosthetic components and for colntolling the motion of the prosthetic components relative to one another to reduce a change for injury.

SUMMARY OF THE INVENTION

The invention is described herein prosthetic components for total ankle replacement and in terms of a process for preparing the ankle for installing the components and for installing the components.

Thus, in accordance with a first aspect of the invention, a method is provided for replacing an ankle within a foot, with the method comprising: a) attaching a tibial component of an ankle replacement prosthesis having a tibial contact surface to a distal end of a tibia; b) forming a talocalcaneal compound by fusing a talus to a calcaneus within the foot; c) forming a slot within the talocalcaneal compound, following step b), extending from a proximal surface of the talus through the talus and through the calcaneus into a lower posterior portion of the calcaneus, and d) attaching a talocalcaneal component of the ankle replacement prosthesis, having a talocalcaneal contact surface configured to move in contact with the tibial contact surface, to the talocalcaneal compound with a stem of the talocalcaneal component extending through the slot formed in step c) within the talocalcaneal compound from the proximal surface of the talus through the talus and through the calcaneus into a lower posterior portion of the calcaneus. For example, the talus is fused to the calcaneus by fusing the suibtalar joint using a screw extending within the talus and the calcaneus.

The method may additionally comprise, before steps a) and b), exposing a proximal surface of the talus and a distal end of the tibia through an anteriolateral longitudinal incision starting about 10 cm above the ankle extending distally over the neck of the talus and being directed laterally and distally to end just below the lateral malleolus, with. neurovascular structures and anterior tendons being retracted medially after longitudinal incision of the superior and inferior ankle retinaculum, and/or performing an osteotomy of the distal fibula with a distal portion of the fibula remaining attached to ligaments within the foot while the tibia is rotated in a posterior direction away from the foot.

The method may additionally comprise, before steps a) and b), performing an osteotomy of the distal fibula with a distal portion of the fibula remaining attached to ligaments within the foot while the tibia is rotated in a posterior direction away from the foot. Then, after step d), the method may additionally compose: repairing the fibular osteotomy temporarily by clamping the osteotomy surfaces together; testing the ankle replacement prosthesis for function, position, and stability; making an adjustment to the ankle replacement prosthesis; and repairing the fibular osteotomy permanently by fastening the osteotomy surfaces together with a plate and screws. The adjustment to the ankle replacement prosthesis may be made with a trail version of the ankle replacement prosthesis, with the trial version being replaced with a permanent version of the ankle replacement prosthesis before the fibular osteotomy is permanently repaired.

The adjustment to the ankle replacement prosthesis may include rotating a head, including the talocalcaneal contact surfaces and a socket attached to a neck within the talocalcaneal component, on the neck, with the socket being eccentrically disposed relative to the talocalcaneal contact surfaces. The adjustment may include replacing the head within the talocalcaneal component with another head having a different level of eccentricity. The adjustment may include replacing a head, including the talocalcaneal contact surface and a socket attached to a neck within the talocalcaneal component, extending to a first depth within the head, with another head having a socket configured to engage the neck at a second depth within the head, significantly different from the first depth.

Step c) of the method may be preceded by removing a predetermined thickness of bone from a crown of the talus to form a talar plafond. For example, the predetermined thickness of bone may be removed from the crown of the talus by a method comprising: clamping the foot within a foot holding fixture to be held with surfaces of a sole of the foot against a main plate; moving a guide plate disposed parallel to the main plate toward the main plate until a talus contacting surface, attached to the guide plate and spaced away from the guide plate through a first distance, contacts the crown of the talus; removing the talus contacting surface from the guide plate; and removing bone having a thickness equal to the first distance from the crown of the talus using a saw moving along the guide plate. Preferably, step c) is additionally preceded by: attaching a paddle guide extending adjacent the talar plafond to bones within the foot; and tracing an edge of a slot within the paddle guide to form a marking on the talar plafond indicating a location and angle for forming the slot within the talocalcaneal compound.

Step a) of the method may be preceded by forming a conical cavity extending within a distal portion of the tibia in a proximal direction from a distal end of the tibia for accepting a conical hub portion of the tibial end of the ankle replacement prosthesis. Step a) may additionally be preceded by removing a predetermined thickness of bone from an inferior articular surface of the tibia to form a tibial plafond. For example, this material may be removed by a method comprising: fastening a tibial guide to the tibia with a contact surface of the tibial guide in contact with the inferior articular surface of the tibia; and removing bone having a thickness equal to a second distance from the interior articular surface of the tibia using a saw operating within a slot within the tibial guide spaced away from the contact surface in the tibial guide by a distance equal to the second distance.

In accordance with a second aspect of the invention, an ankle replacement prosthesis is provided. comprising: a tibial component having a tibial contact surface; and a talocalcaneal component including a head having a talocalcaneal contact surface, movable in contact with the tibial contact surface, and a stem configured to be held within a slot within a talocalcaneal compound formed by fusing a talus and a calcaneus, wherein the stem is configured to extend from the head within the slot through the talus and through the calcaneus to a lower posterior portion of the calcaneus.

Preferably, the head is attached to the stem by a cavity within the head engaging a neck extending from the stem, with the head being selected from a plurality of heads having cavities engaging the neck at different distances within the heads. The plurality of heads may additionally have cavities disposed at a plurality of different levels of eccentricity relative to the talocalcaneal contact surfaces. The tibial contact surface and the talocalcaneal contact surface may each be spherical, or these contact surfaces may include mating features that limit inversion/eversion rotation while providing for dorsal/plantar rotation. For example, the tibial contact surface and the talocalcaneal contact surface may each include portions rounded in anterior/posterior directions and straight in medial/lateral directions, providing relative rotation between the tibial component and the talocalcaneal component, and flat portions extending in anterior/posterior directions to prevent relative medial/lateral movement between the tibial component and the talocalcaneal component.

Preferably, the tibial component of the ankle replacement prosthesis includes a hub having a conical surface for absorbing stress from the tibia in a manner maintaining stress levels consistent with longevity in the surrounding bone matter of the tibia.

BRIEF DESCRIPTION OF THE FIGURES

These and other aspects of the invention will be made apparent by reading the following specification in conjunction with the accompanying drawings, in which:

FIG. 16 is a medial cross-sectional view of the talocalcaneal compound of FIG. 14, showing the enlargement of the hole formed shown in FIG. 14 with a chisel;

FIG. 17 is a medial cross-sectional view of the talocalcaneal compound of FIG. 14, showing the formation of the slot for receiving the stem within the ankle replacement prosthesis of FIG. 1 using a rasp;

FIG. 18 is a medial cross-sectional view of the talocalcaneal compound of FIG. 14, showing the insertion of the stem within the ankle replacement prosthesis of FIG. 1 into the slot formed in FIG. 17, FIG. 19 is a fragmentary cross-sectional medial view of the tibia within the bone structure of FIG. 1, showing the formation of a socket for receiving the tibial component within the ankle replacement prosthesis of FIG. 1;

FIG. 20 is a fragmentary, partly sectional medial view of the talocalcaneal component within the aml;e replacement prosthesis of FIG. 1, showing the attachment of a head therein;

FIG. 21 is a fragmentary transverse cross-sectional plan view of head and neck within the talocalcaneal component of FIG. 20;

FIG. 22 is a fragmentary, partly sectional medial view of the talocalcaneal component of FIG. 20, showing the attachment of an alternative head therein;

FIG. 23 is a medial view of an ankle replacement prosthesis built in accordance with a first version of a second embodiment of the invention;

FIG. 24 is a partially sectional posterior view of the prosthesis of FIG. 23;

FIG. 25 is a partly sectional medial view of an ankle replacement prosthesis built in accordance with a second version of the second embodiment of the invention;

FIG. 26 is a partially sectional posterior view of the prosthesis of FIG. 25;

DETAILED DESCRIPTION OF THE INVENTION

Figure 1:
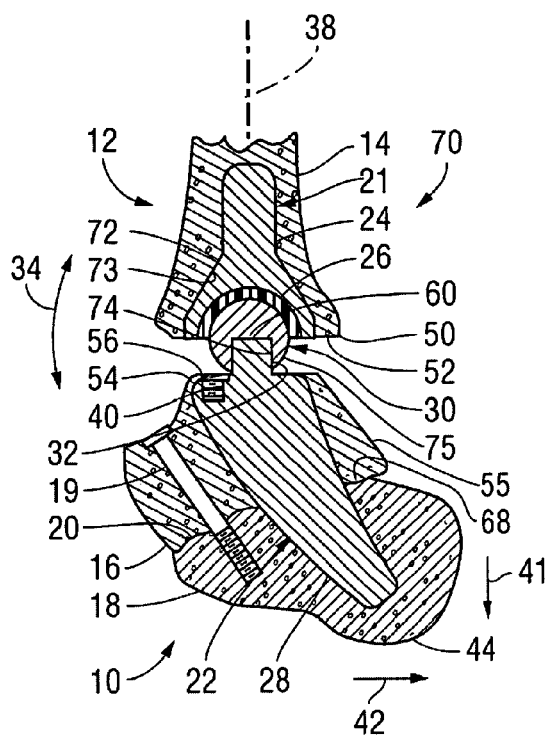
FIG. 1 is a fragmentary medial cross-sectional elevation of a bones in the ankle area having an ankle replacement prosthesis made and installed in accordance with a first embodiment of the invention.

FIG. 1 is a fragmentary medial cross-sectional elevation of a bone structure 10 having an ankle replacement prosthesis 12 made and installed in accordance with the invention. The bone structure 10 includes a distal end of a tibia 14, a talus 16, and a calcaneus 18. During the process of installing the prosthesis 12, the talus 16 and the calcaneus 18 are fused together using a screw 19, forming a selective, primary fusion of the subtalar joint 20. The prosthesis 12 includes a tibial component 21, attached to the tibia 14, and a talocalcaneal component 22, attached to the talus 16 and to the calcaneus 18. In turn, the tibial component 21 includes a hub 24 holding a socket 26, while the talocalcaneal component 22 includes a stem 28, to which a head 30 is attached by a neck 32, with the stem 28 being inserted through the talus 16 into the calcaneus 18. The head 30 is rotatable in all directions within the socket 26, providing for planter/dorsal flexure in the directions of arrow 34, for flexure in the inversion/eversion directions of arrows 36, and for axial rotation about axis 38. A threaded socket 39 is provided within the stem 28 to hold the stem 28 during installation.

Figure 2:
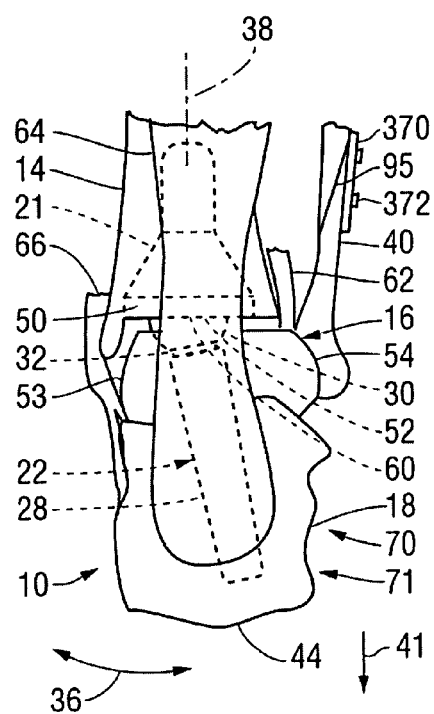
FIG. 2 is a posterior elevation of the bone structure of FIG. 1 with the ankle replacement prosthesis installed therein.

FIG. 2 is a posterior view of the bone structure 10, additionally including a fibula 40, showing the placement of the prosthesis 12. The stem 28 is curved, as shown in FIG. 1, extending from the neck 32, downward, in the direction of arrow 41 and in the posterior direction of arrow 42, and tapered at 1.5 degrees, as shown in FIG. 2, extending from the neck 32, downward and in the lateral direction of arrow 43. When the head 30 transmits reaction forces, particularly arising from the weight of the patient, to the neck 32, the stem 28, with its curved shape, transmits these forces from the neck 32 to the lower posterior section 44 of the calcaneus 18, which is the anatomically normal weight bearing section of the calcaneus 18. The tapered and curved shape of the stem 28 also provides firm fixation with both the talus 16 and the calcaneus 18, reinforcing the fusion provided by the screw 19. The relatively thin posterior shape of the stem 28 allows the talocalcaneal component 24 to occupy a small portion of the volume of the body of the talus 16, with the stem 28 having minimal impact on the flow of blood through the talus 16, reducing the risk of avascular necrosis.

A process for preparing the bone structure 10 for the installation of the prosthesis 12 includes removing material from the distal end 50 of the tibia 14 to form a tibial plafond 52 and with removing material from the superior dome 54 of the talus 16 to form a talar plafond 56, which are configured so that, when the prosthesis 12 is installed, these plafonds 52, 56 are spaced apart by a distance of 6 mm, providing clearance for flexural movement of the tibia relative to the talus in the directions of arrows 34, 36, and further forming datum surfaces that are used as references in shaping additional surfaces within the bone structure 10. Because of a need for accuracy in forming the plafonds 52, 56, rigid fixturing is provided for holding the bone structure 10 is place and for establishing the required locations of the plafonds 52, 56. A very thin layer of material is removed from the superior dome 54 of the talus 16 to form the talar plafond 56, preserving over 90 percent of the mass of the talus 16, with the medial boundary 53 thereof, the lateral boundary 54 thereof the posterior boundary 55 and all muscles and ligaments remaining intact. Since these boundaries 53, 54, 55 are left intact, the talus 16 remains in an anatomically correct position in respect to the mortis 56, assuring stability of the ankle joint 58 and providing nearly normal anatomically functional properties.

The prosthesis 12 provides ball-and-socket articulation at a point 60 above the talus. The Achilles tendon 64, medial ligaments 66, lateral ligaments 67, and the mortis 68 provide stability in performing these functions in an anatomically normal manner. The ball-and-socket articulation does not transfer shear forces or torques between the socket 26 and the head 30 and the reaction force caused by body weight is shared by the talus 16 and the calcaneus 18, assuring longevity of the construct 70 formed by the bones 14, 16, 18 and the prosthesis 12.

Furthermore, the tibial component 21 is configured to disperse stresses resulting from the application of the weight of the patient to the foot 71 from a large conical surface 72 onto the matching prepared surface 73 within the tibia 14, allowing force to be transferred in a unified manner onto the tibia 14. The self-centering conical surface 70 further minimizes the transfer of rotational or shearing forces through the interfaces between the bones 14, 16, 18 and the prosthesis 12, providing longevity of the construct 70.

In accordance with a first embodiment of the invention, both the socket 26 and the head 30 have spherical contact surfaces. The overall configuration of the construct 70 provides for planter/dorsal flexure in the directions of arrow 34, for flexure in the inversion/eversion directions of arrows 36, for axial rotation about axis 38 and for varus/valgus motion to occur in manners closely simulating normal anatomical ankle movement. The ligaments and soft tissue of the ankle, which remain intact during the installation of the prosthesis 12, freedom of movement and stability at the anatomical level. While subtalar movement has been prevented by fusing the talus 16 with the calcaneus 18, such movement is simulated by the movements available between the head 30 and the socket 26.

In accordance with a first embodiment of the invention, both the

In accordance with a preferred version of the invention, several versions of the head 30 are provided as a kit, with variations among the versions occurring in the form of variations in a level of eccentricity between neck receiving hole 74, configured to engage the neck 32, and an outer surface 75 of the head 30, and with variations additionally occurring in the shape of the neck receiving hole 74 to change the level to which the pin 32 extends into the head 30. Such variations can be used to adjust the operation of a particular prosthesis 12 installed in accordance with the invention in a particular patient before completing the required surgical procedures.

For example, the socket 26 is composed of an ultra-high-molecular-weight polyethylene resin, while other components are composed of a cobalt/chromium/molybdenum alloy, of commercially pure titanium, or of stainless steel.

Figure 3:
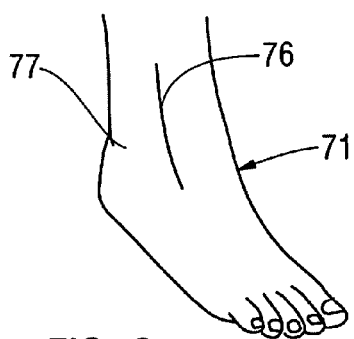
FIG. 3 is a perspective view of a foot, showing an incision that is performed to begin exposure of the tibia and talus therein.

FIG. 3 is a perspective view of the foot 71, showing an anteriolateral longitudinal incision 76 that is performed to begin a process of exposing portions of the tibia 14 and the talus 16 as required for installing the prosthesis 12 in accordance with the invention. For example, the method described in *Operative Approach in Orthopedic Surgery and Traumatology*, by R. Bauer, F. Kerschbaumer and S. Poisel, published by Thieme Medical Publishers, Inc., New York, 1987, pages 174-176 may be used, beginning with making the incision 76, starting about 10 cm above the ankle 77, and extending distally over the neck of the talus and being directed laterally and distally to end just below the lateral malleolus, with. neurovascular structures and anterior tendons being retracted medially after longitudinal incision of the superior and inferior ankle retinaculum.

Figure 4:
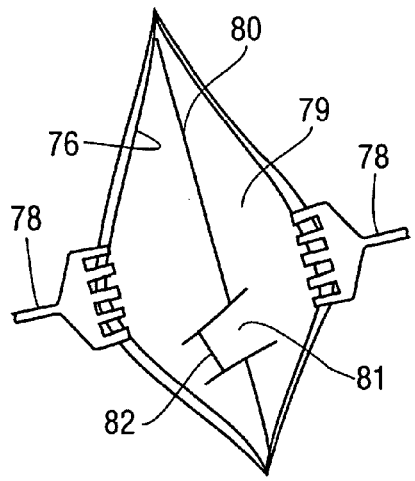
FIG. 4 is a first perspective view of the incision of FIG. 3.

FIG. 4 is a first perspective view of the incision 76, showing a method for exposing the ankle. As shown in FIG. 4, after splitting the skin and subcutis to form the incision 76, which is held open with retractors 78, the Crural fascia 79 is divided with a straight incision 80 and the inferior extensor retinaculum 81 is divided with an H-shaped incision 82, with care being taken not to damage the branches of the superficial peroneal nerve lying medial to this incision.

Figure 5:
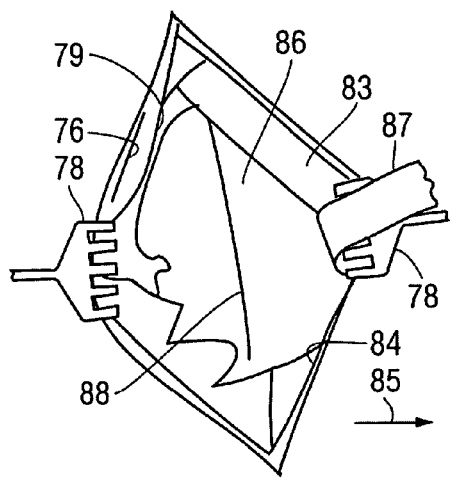
FIG. 5 is a second perspective view of the incision of FIG. 3.

FIG. 5 is a second perspective view of the incision 76, sequentially following FIG. 4. As shown in FIG. 5, the long extensor muscle 83 to the toes and a tendon 84 of the third peroneal muscle are retracted in the medial direction of arrow 84a, while the Crural fascia 79 is retracted in the lateral direction, opposite the direction of arrow 84a. Transverse venous branches of the lateral anterior malleolar artery (not shown) are ligated and transected. With the aid of a raspatory the neurovascular bundle (not shown) can be cautiously retracted in the medial direction of arrow 85 from the anterior aspect of the ankle joint capsule 86. Then, a Langenbeck retractor 87 is inserted in the same plane, and the ankle joint capsule 85 is split with a longitudinal incision 88.

Figure 6:
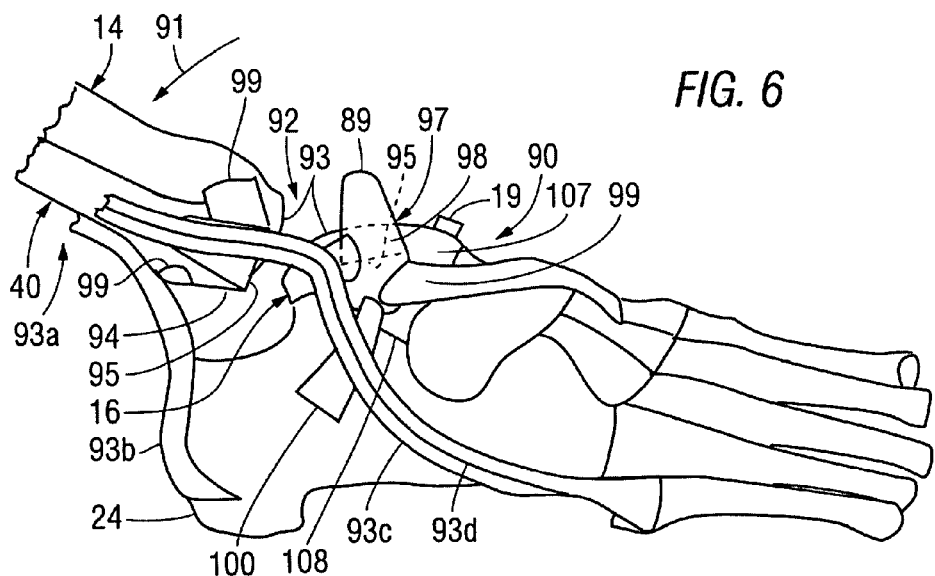
FIG. 6 is a fragmentary lateral elevation of bones and ligaments in the ankle area during the process of preparing to install the ankle replacement prosthesis of FIG. 1.

FIG. 6 is a fragmentary lateral elevational view of bones and ligaments in the ankle area, shown following an osteotomy of the fibula 40 and fusion of the talus 18 and the calcaneus 18. In accordance with the present invention, these procedures are performed following the process described above to expose the ankle. Following the osteotomy, the distal fibula 89 remains with the foot 71, together with associated ligaments 90, which remain intact. This procedure allows the tibia 14 to be rotated posteriorly, in the direction of arrow 91, with a space 92 being opened between the formerly adjacent surfaces 93 of the tibia 14 and the talus 16, so that these surfaces 93 can be shaped as required for installation of the prosthesis 12. Various flexible structures extending between the foot 71 and the leg 93a, including the Achilles tendon 93b, the fibularis (peroneus) longus tendon 93c, and the fibularis (peroneus) brevis tendon 93d. The talus 16 and the calcaneus 18 are fused together by the insertion of a screw 19.

The osteotomy of the fibula 40 begins as the periosteum of a distal portion 89 of the fibula 40 is incised anteriorly and longitudinally and is elevated, with a subperiosteal osteotomy then being performed on the distal portion 89 of the fibula 40 in a long, oblique fashion starting at the distal end 94 of the tibiofibular syndesmosis medially, extending laterally and proximally to provide a large osteotomy surface 95 while preserving the distal tibiofibular joint (syndesmosis) 96. The distal portion 97 of the osteotomy, including the distal fibula 89 and lateral malleolus 98, is retracted laterally and distally leaving the talofibular ligaments 99 and calcaneofibular ligament 100 intact.

Figure 7:
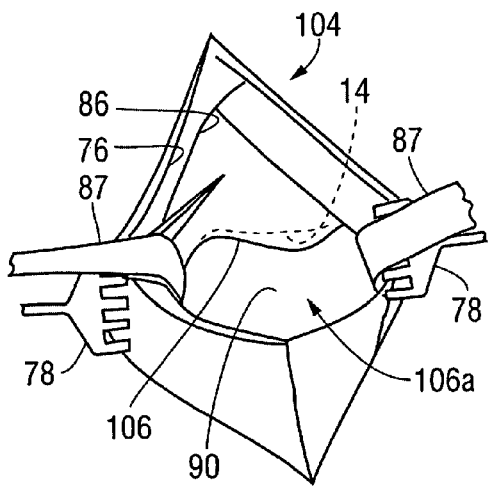
FIG. 7 is a third perspective view of the incision of FIG. 3.

FIG. 7 is a third perspective view of the incision 76, showing the liberal exposure of the ankle joint 102, with the anterior capsule 85 and the ankle 102 being released subperiosteolly and longitudinally. The posterior ankle joint 104 is released transversely, and the talus 18 is exposed, with the periosteum 106 of the tibia 14 proximal to the capsule 85 being split and. retracted with a raspatory in the same plane as the capsule 85. Then, Langenbeck hooks 87 are inserted into the joint, exposing the trochlea 106 of the talus 18 as well as the distal end of the tibia 14.

Then, referring again to FIG. 6, with careful dissection, the neck 107 of the talus 16 and the subtalar joint 108 are exposed. Using a bur, the articular surfaces of the subtalar joint 108 are decorticated keeping the talus 16 and calcaneus 18 in correct anatomical portion relative to each other. Primarily subtalar fusion is initiated by insertion of a screw 19 through the neck 107 of talus 16 into the calcaneus 18 to fix the talus 16 to the calcaneus 18. The position is confirmed under fluoroscopy.

Figure 8:
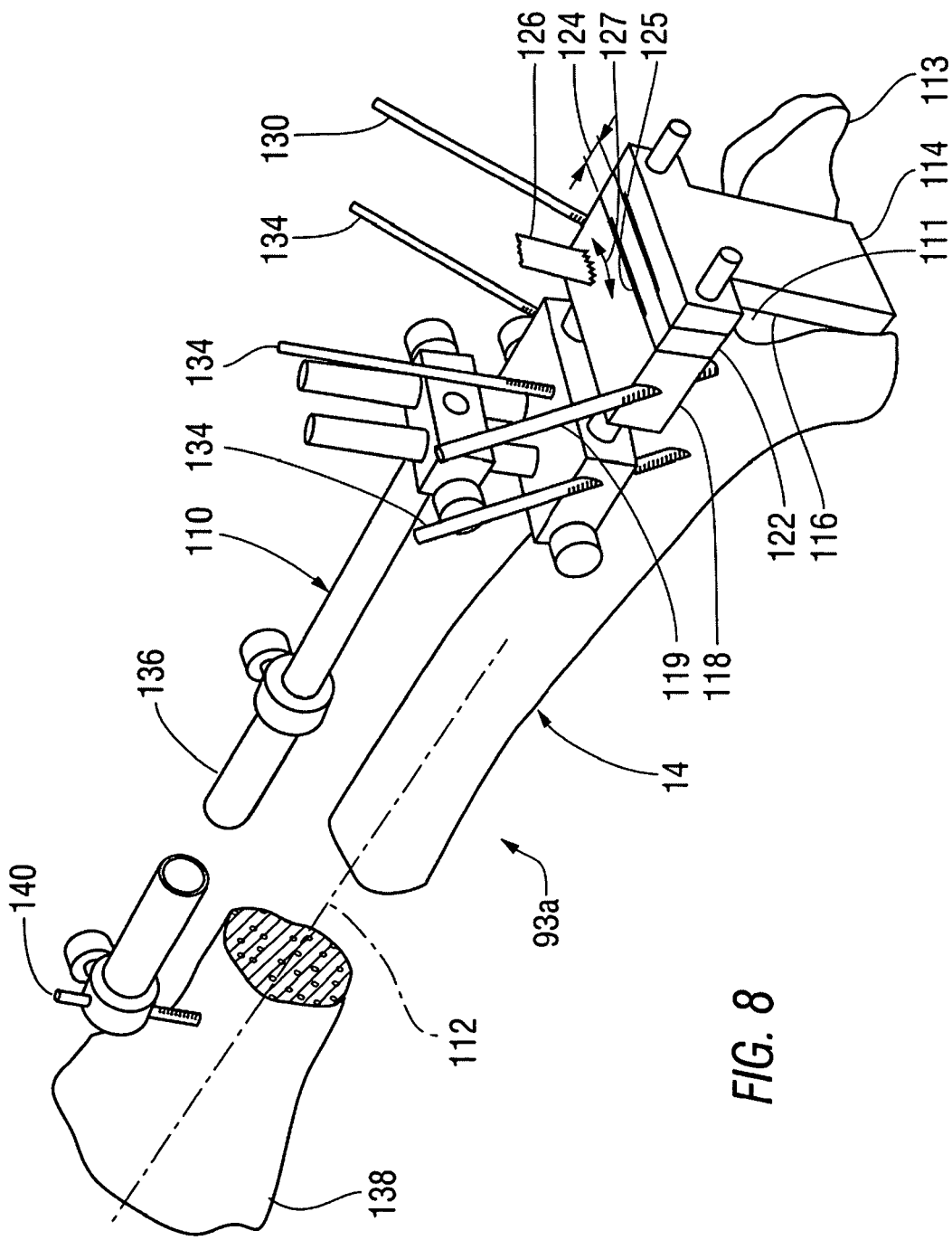
FIG. 8 is a fragmentary perspective view of a tibial guide used in a process of cutting a tibial plafond for installing a tibial component within the ankle replacement prosthesis of FIG. 1.

FIG. 8 is a fragmentary perspective view of a tibial guide 110, which is fastened in place over the anterior aspect of the tibia following the processes described above in reference to FIGS. 3-7. Using a tibial guide 110, the tibial inferior articular surface 111 is cut perpendicular to the long axis 112 of the tibia, to form the tibial plafond 52 described above in reference to FIG. 1. About 4 mm is removed from the tibial inferior articular surface 111 while the medial malleolar 113 left intact. In this figure, the tibial guide 110 is shown in its relationship with the tibia 14, to which the fixture is attached, without showing the other elements of the leg 93a. The tibial guide 110 includes a contact plate 114 having a contact surface 116 that is held in contact with the inferior articular surface 117 of the tibia 14, as a distal mounting block 118 of the tibial guide 110 is fastened into place with a pair of bone screws 119 extending into the tibia 14. A spacing plate 122 disposed between the contact plate 114 and the distal mounting block 118 establishes a distance 124 between the contact surface 116 and a slot 125, which is used to guide an oscillating saw blade 126, driven in the directions of arrow 127. Other elements within the tibial guide 110, which are provided to stabilize the distal mounting block 118 relative to the tibia 14, include an intermediate mounting block 132, which is attached to the tibia 14 by three bone screws 134, and a telescoping tube 136, which is attached to the tibia 14 near its proximal end 138 by a single bone screw 140. These elements are adjustably connected to one another so they can be configured to accommodate variations in examples of the tibia 14 that may be encountered. After the tibial guide 110 is attached to the tibia 14, the oscillating saw blade 108 is moved into contact with the tibia 14 through the slot 116, and is moved through the tibia 14 with the saw blade 108 being driven in the directions of arrow 110, removing a portion of the tibia 14 having a thickness determined by distance 124. Then, the tibial guide 110 is removed from the tibia 14.

Figures 9, 10, 11:
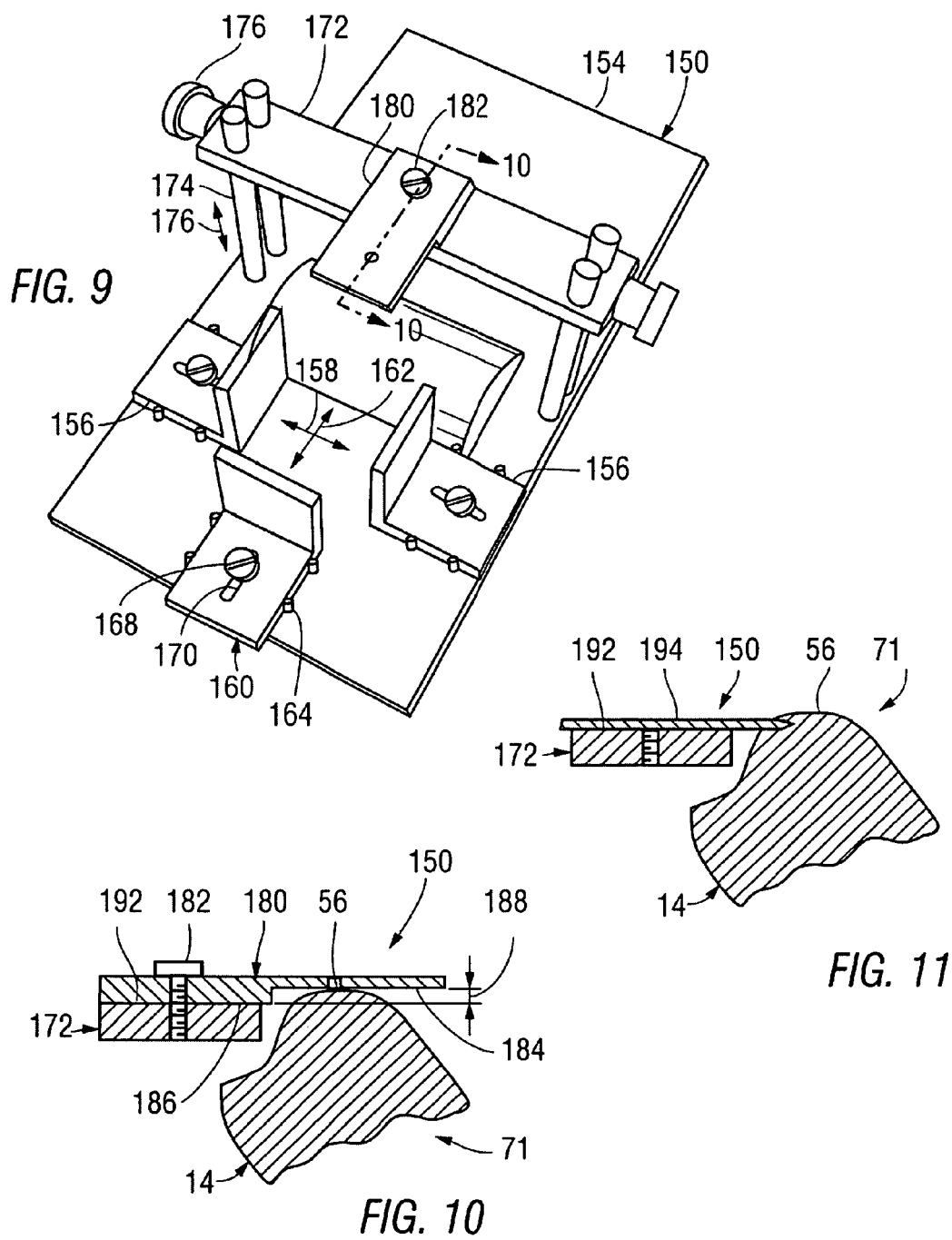
FIG. 9 is a perspective view of a foot holding fixture used in a process of cutting a talar plafond for installing a talocalcaneal component within the ankle replacement prosthesis of FIG. 1.
FIG. 10 is a fragmentary cross-sectional elevation of the foot holding fixture of FIG. 9, taken as indicated by section lines 10-10 therein to show a relationship between a guide plate within the fixture and the talus of a foot held within the fixture.
FIG. 11 is a fragmentary cross-sectional elevation of the foot holding fixture of FIG. 9, showing the cutting of the talar plafond therein.

FIG. 9 is a perspective view of a foot holding fixture 150, which is used to remove, for example, 3 mm of the superior dome 54 of the talus 16 is cut parallel to a surface simulating a floor on which the patient is standing. The foot holding fixture 150 includes a main plate 154, a pair of side brackets 156, each movable in the directions of arrow 158 along the main plate 154, and a heel bracket 160, movable in the directions of arrows 162 along the main plate 154. Each of the brackets 156, 160 is constrained to move between a number of guide pins 164, with clamping screws 168 extending through slots 170 being provided to clamp the brackets 156, 160 in place. The foot holding fixture 150 further includes a curved support bar 171, which is attached to the main plate 154. These features of the foot holding fixture are adjusted and used to hold the foot 71 (shown in FIG. 3) firmly in place during the processes of reshaping the talus 16, and during the subsequent installation of the talocalcaneal component 22 within the talus 14 and the calcaneus 18. The foot holding fixture 150 additionally includes a guide plate 172, which is spaced away from the main plate 154, being movable perpendicular to the main plate 154 in the directions of arrow 174 along mounting posts 176. Clamping knobs 178 are pivoted to clamp and to release the guide plate 172 for movement along the mounting posts 176. A guide bracket 180 is removably attached to the guide plate 172 by a screw 182.

FIG. 10 is a fragmentary cross-sectional elevation of the foot holding fixture 150 with the foot 71 clamped therein, taken as indicated by section line 10-10 in FIG. 9, to show a relationship between the guide plate 172 and the talus 14 forming a portion of the foot 71. The guide bracket 180 includes a talus contacting surface 184 and a plate contacting surface 186, which are spaced apart by a distance 188. With the foot 71 clamped in place within the fixture 190 as described above in reference to FIG. 10, the guide plate 172 is moved along the mounting posts until the talus contacting surface 184 comes into contact with the crown 190 of the talus 14. Then the clamping knobs 178 are pivoted to clamp the guide plate 172 in place, and the guide bracket 180 is removed.

FIG. 11 is a fragmentary cross-sectional elevation taken as FIG. 10, showing a process for forming the talar plafond 56, using an oscillating saw blade 194 held against the outer surface 192 of the guide plate 172. In this process, the properties of the foot holding device 150 ensure that the talar plafond 56 is properly aligned and located. Specifically, since the foot 71 is clamped to be held against the main plate 154 in a manner simulating the foot being held against a flat, horizontal floor surface, while the support columns 174 hold the outer surface 192 of the guide plate 172 parallel to the main plate 154, the process forms the talar plafond 56 to be parallel to a floor surface on which the patient will later be standing. Furthermore, since the guide plate 180 is configured to place the outer surface 192 of the guide plate inward, in the direction of arrow 194 through the distance 188 from the outermost portion of the superior dome 56, it is understood that the tibial plafond is placed at this distance 188 from the former location of the outermost portion of the superior dome 56.

Figure 12:
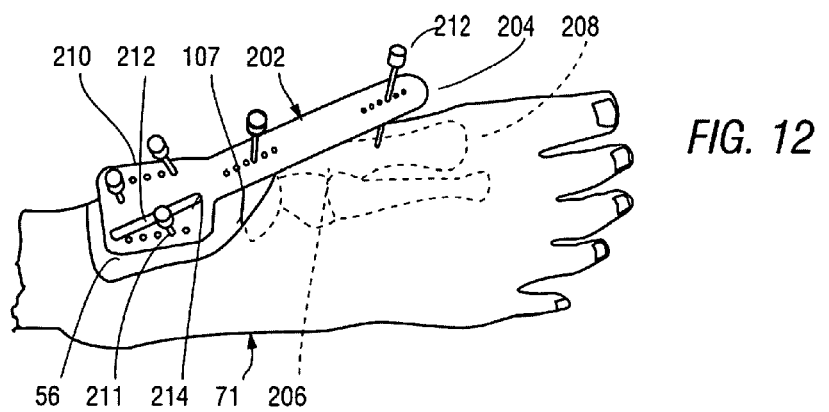
FIG. 12 is a dorsal view of the foot during the use of a tibial guide to determine the placement on the talar plafond of a slot for receiving a stem within a talocalcaneal component of the ankle replacement prosthesis of FIG. 1.

FIG. 12 is a dorsal view of the foot 71 following the process of forming the tibial plafond 56 as described above in reference to FIG. 11 and during a process determining the placement of a slot 200 within the talus 16 and the calcaneus 18 for insertion of the talocalcaneal component 22 as shown in FIG. 1 begins with placing the talar paddle guide 202 over the foot 71 so that a handle 204 of the talar paddle guide 202 is passed over the head and neck 107 of the talus 16 and over the base 206 of the first metatarsal 208. The paddle part 210 of the talar paddle guide 202 then seats on the talar plafond 56 of the osteotomized body of the talus 16. The talar paddle guide 202 is then temporarily fixed to the base 206 of the first metatarsal 208 and to the /neck 107 of talus 16 and to the body of talus 16 with the provided bone pins 212. The talar paddle guide 202 includes a number of holes 211, which are provided so that the guide 202 can be properly installed despite variations in the bone structure of the foot 71, and a slot 212, which overlays the location where the slot 200 is to be formed. Thus, the edge 214 of the slot 212 is traced onto the talar plafond 56 with a pen before the tallar paddle guide 202 is removed from the foot 71.

Figure 13:
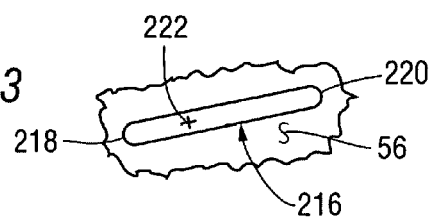
FIG. 13 is a fragmentary dorsal view of the talar plafond formed as shown in FIG. 11, showing a marking formed as shown in FIG. 12.

FIG. 13 is a fragmentary dorsal view of the talar plafond 56 showing a marking 216 formed thereon by tracing the edge 214 of the slot 212 within the talar paddle guide 202. The marking 216 extends from an anterior end 218 to a posterior end 220 at an angle indicating the angle at which a slot is to be cut for receiving the stem 28 of the talocalcaneal component 22, shown in FIG. 1. A target point 222, at one third the distance from the anterior end 218 of the marking 216 to the posterior end 220 thereof is to be used as a center for drilling a hole within the talus 16 and the calcaneus 18.

Figure 14:
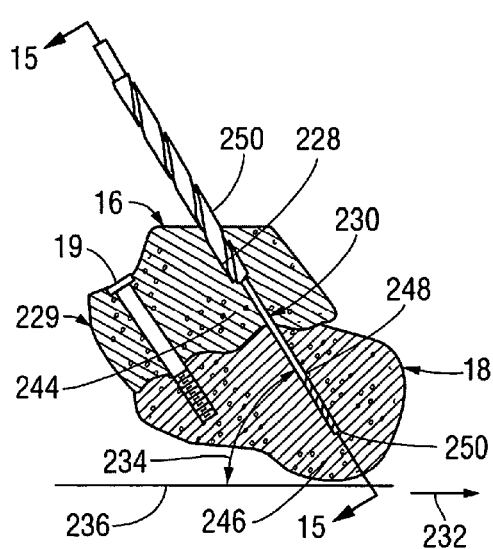
FIG. 14 is a medial cross-sectional view of a talocalcaneal compound formed within the bone structure of FIG. 1, showing the drilling of a hole therein, beginning the process of forming the slot for receiving the stem within the ankle replacement prosthesis of FIG. 1.
Figure 15:
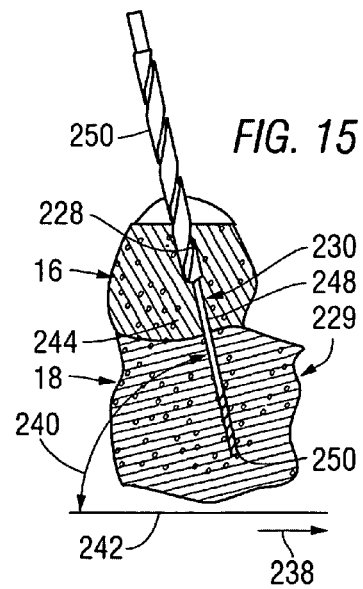
FIG. 15 is a posterior cross-sectional view of the talocalcaneal compound of FIG. 14, taken as indicated by section lines 15-15 therein.

A process for drilling a hole 228 to begin the process of forming a slot for placement of the stem 28 will now be discussed, with reference being made to FIGS. 14 and 15. FIG. 14 is a cross-sectional medial elevation of the talus 16 and the calcaneus 18, which have been fused as described above with the screw 19 to form a talocalcaneal compound 229, while FIG. 15 is a cross sectional posterior elevation thereof, taken as indicated by section lines 15-15 in FIG. 14. First, a 3-mm diameter guide wire 230 is inserted with a drill, starting at the target point 222, with the guide wire 230 being directed downward and in the posterior direction of arrow 232 at an angle 234, which is about 45 degrees to a surface 236 contacting the sole of the foot 71 to simulate a floor surface, as shown in FIG. 14. As shown in FIG. 15, the guide wire 230 additionally extends downward and in the lateral direction of arrow 238, being inclined at an angle 240 of 75 to 80 degrees with a line 242 extending along the surface 236 in the lateral direction of arrow 238. Thus, the guide wire 230 is directed through the midportion 244 of the body of the talus 16 into the calcaneus 18 and to the posterior weight bearing portion 246 of calcaneus 18. Proper positioning of the guide wire 230 is confirmed under fluoroscopy. Then, the length of a portion 248 of guide wire 230 inserted into the bones 15, 18 is measured and a stop on a cannulated drill tip 248 is adjusted, allowing the cannulated drill top 248 to be driven along the guide wire 230 to the distal end 250 thereof, forming a drill hole 250 within the talocalcaneal compound 229. The position of the drill tip 248 is evaluated under fluoroscopy. Finally, the drill 248 and the guide wires 230 are removed.

FIG. 16 is a cross-sectional medial elevation of the talocalcaneal compound 229 showing the use of a chisel 260 to enlarge the hole 228 therein formed by drilling, as described above in reference to FIGS. 14 and 15. The chisel 260 includes four sharp points 262 for removing bone particles and a cylindrical anvil 264 that is tapped using a hammer (not shown). During the process of enlarging the hole 228, the marking 216, formed as described above in reference to FIG. 12, is used to assure that a slot 266 being formed is configured to extend at the proper angle within the talocalcaneal compound 229.

FIG. 17 is a cross-sectional medial elevation of the talocalcaneal compound 229 showing the use of a rasp 270 to enlarge the slot 266 formed using the chisel 260 as described above in reference to FIG. 16. The rasp 270 includes a removable blade portion 272 and a handle portion 274, which extends to a cylindrical anvil 276 that is tapped using a hammer (not shown). The blade portion 272 includes bone cutting teeth 278 extending along its peripheral edge 280 and bone cutting teeth 282 extending along its sides 284. The blade portion 272 is shaped to make the final cut forming a slot 286 configured to accept the stem 28 of the talocalcaneal component 22 of the prosthesis 12 (shown in FIG. 1). Preferably, the slot 286 is formed in several stages using several rasps with blade portions differing in size and shape and different types of cutting surfaces. For example, the slot 282 may be formed by first using a first rasp with a blade portion having a profile indicated by a dashed line 288, by then using a second rasp with a blade portion having a profile indicated by another dashed line 290, and by finishing the slot 286 with the rasp 270. Again, the marking 216 is used to assure the slot 286 is formed to extend at the proper angle within the talocalcaneal compound 229.

FIG. 18 is a cross-sectional medial elevation of the talocalcaneal compound 229 showing the insertion of the stem 28 into the slot 282, which has been prepared as described above in reference to FIG. 17. The stem 28 is held and moved using an insertion tool 300, having a threaded tenon 302 engaging the threaded socket 39 (shown in FIG. 1) within the stem 28. The insertion tool 300 additionally includes a handle portion 304 extending to a an anvil 306, which is tapped with a hammer.

FIG. 19 is a fragmentary cross-sectional medial elevation of the tibia 14, showing a socket 320 being formed therein to extend inward, in the proximal direction of arrow 322, from the tibial plafond 52, which has been formed as described above in reference to FIG. 8. The process of forming the socket 320 begins with inserting a 3-mm diameter guide wire 324 into the center of the tibial plafond using a drill, with a hole 328 then being formed to extend in the proximal direction of arrow 322, staying as close as possible to the long axis 330 of the tibia 14. The tibial reamer 332 is then inserted over the guide wire 324, being driven in rotation along the guide wire 324 to form the socket 320. The tibial reamer 332 includes a central tube 333, which is inserted over the guide wire 324, a first plurality of flutes 334 configured to form a cylindrical opening 336, a second plurality of flutes 338 configured to form a conical opening 340, and a ridge 342 configured to stop movement of the tibial reamer 332 in the proximal direction of arrow 322 when the socket 320 has been formed.

FIG. 20 is a fragmentary cross-sectional medial elevation of the talocalcaneal component 22 of the prosthesis 12, showing the attachment of a preferred version of the head 30 to the neck 32 therein. Both the peripheral surface 350 of the neck receiving hole 74 within the head and the peripheral surface 352 of the neck 32 are tapered at an angle 353, which is preferably 1.5 degrees, so that the peripheral surfaces 350, 352 are self locking, in the manner of a Morse taper, when a sufficient force is applied to the head 30 in the distal direction of arrow 354. In the example of FIG. 20, the neck receiving hole 74 and the outer surface 355 of the head 30 are coaxial, being aligned along a common axis 356.

FIG. 21 is a fragmentary transverse cross-sectional view of the head 30 and the neck 32 within the talocalcaneal component 22, taken as indicated by section lines 21-21 in FIG. 20, showing portions of the peripheral surfaces 350, 352, which each have a pattern 358 of grooves and ridges. The patterns 358 of the peripheral surfaces 350, 352 at least partially interlock to prevent relative axial rotation, in the direction of arrow 353, between the head 30 and the neck 32 after the head 30 is locked in place on the neck 32.

FIG. 22 is a fragmentary cross-sectional medial elevation of the talocalcaneal component 22 showing the attachment of an alternative head 354 to the neck 32. The alternative head 354 includes a neck receiving hole 356 that is deeper, in the proximal direction of arrow 362, than the neck receiving hole 74 in the head 30. Additionally, the neck receiving hole 356 has an axis 364 that is displaced through an eccentric distance 366 from the axis 368 of the outer surface 370 of the alternative head 354. In accordance with a preferred version of the invention, a kit including a heads having plurality of different eccentricities and a plurality of different neck receiving hole depths is provided for use within the talocalcaneal component 22. For example, such a kit may include heads having eccentricities of 0, 1, 2, and 3 mm, with such variations being used to adjust the operation of a particular prosthesis 12 installed in accordance with the invention in a particular patient before completing the required surgical procedures.

In accordance with a preferred version of the invention, after the slot 286 is formed within the talocalcaneal compound 229, a trial version of the talocalcaneal component 22 is inserted into the slot 286, in the manner described above in reference to FIG. 18. Then, the head 30, having preferably been selected from a group of heads having differing eccentricities and hole depths, as described above in reference to FIG. 22, is seated on the neck 32 of the talocalcaneal component 22 as shown in FIG. 20. Additionally, after the socket 320 has been formed within the distal end of the tibia 14, as described above in reference to FIG. 20, a trial version of the tibial component 21 is inserted within the socket 320. It does not matter whether the tibial component 21 is inserted before of after the head 30 is seated on the neck 32. After the tibial component 21 has been thus inserted and after the head 30 has been seated on the neck 32, the head 30 is brought into engagement with the trial version of the tibial component 21, forming a trial version of the prosthesis 12. Then, the osteotomy of the fibula 40 is reduced, with the osteotomy surfaces 95 (shown in FIG. 6) being brought together to be temporally held together with a clamp (not shown). Then, the function, position, and stability of the combination of the bone structure of the patient with the trial version of the prosthesis 12 are observed and tested, with adjustments being made as necessary. Such adjustments may include rotating a head having an eccentricity 366, (shown in FIG. 22), the replacement of the head 30 with another head having a different eccentricity 366, and/or having a neck receiving hole 356 with a different depth. When it has been determined that the trial version of the prosthesis 12 works properly, the clamp is removed from the osteotomy of the fibula, allowing the tibia 14 to again be rotated in the direction of arrow 91 (as shown in FIG. 6), and the trial version of the prosthesis 12 is removed, being replaced by the permanent version of the prosthesis 12. Then, as shown in FIG. 1, the fibular osteotomy is then repaired, with the osteotomy surfaces 95 being held together by a plate 370 and screws 372, and the incision 76 is closed in layers, in the usual manner.

In accordance with a second embodiment of the invention, mating features are provided within an ankle replacement prosthesis for limiting inversion/eversion rotation while providing for dorsal/plantar rotation. For example, FIGS. 23 and 24 show an ankle replacement prosthesis 400, built in accordance with a first alternative embodiment of the invention to include means for limiting inversion/eversion rotation, in the directions of arrow 402, to a level much less than a permitted level of dorsal/plantar rotation, in the directions of arrow 404. FIG. 23 is a medial view of the prosthesis 400, while FIG. 24 is a partly sectional posterior view thereof. The ankle replacement prosthesis 400 includes a talocalcaneal component 406 having a stem 408 that extends to the weight bearing portion 246 of the calcaneus 229 within the talocalcaneal compound 229 (all shown in FIG. 14). The ankle replacement prosthesis additionally includes a tibial component 409. The talocalcaneal component 406 additionally includes a pair of flanges 410 extending in the proximal direction of arrow 411 at medial and lateral sides of the head 412 to restrict movement in the directions of arrow 402 by coining into contact with a flange 414 extending outward from a socket 416 within the tibial component 410. Other aspects of the ankle replacement prosthesis 400 are as described above regarding the ankle replacement prosthesis 12.

FIGS. 25 and 26 show an ankle replacement prosthesis 420, built in accordance with a second version of the second embodiment of invention to prevent inversion/eversion rotation, in the directions of arrow 402. FIG. 25 is a partly sectional medial view of the prosthesis 420 while FIG. 26 is a partly sectional posterior view thereof. Again, the ankle replacement prosthesis 420 includes a talocalcaneal component 422 having a stem 424 that extends to the weight bearing portion 246 of the calcaneus 229 within the talocalcaneal compound 229 (all as shown in FIG. 14). The ankle replacement prosthesis 420 additionally includes a tibial component 426. A tibial contact surface 428 of a socket 430 within the tibial component 426 and a talocalcaneal contact surface 431 of a head 432 within the talocalcaneal component 422 are each rounded in the anterior/posterior directions of arrow 433, and are each straight in the medial/lateral directions of arrow 434, permitting relative rotation in the dorsal/plantar directions of arrow 404, while preventing inversion/eversion rotation, in the directions of arrow 402. Relative movement in the medial/lateral directions of arrow 434 is prevented by contact between flat end portions 436 of the tibial contact surface 428 and flat end portions 438 of the talocalcaneal contact surface 431, all of which extend in the anterior/posterior directions of arrow 433. The contact surfaces 428, 431 may be cylindrically curved, or may be curved in the directions of arrow 433 at a radius much larger than their curvature in the directions of arrow 432. Other aspects of the ankle replacement prosthesis 400 are as described above regarding the ankle replacement prosthesis 12, made in accordance with the first embodiment of the invention.

Figure 27:
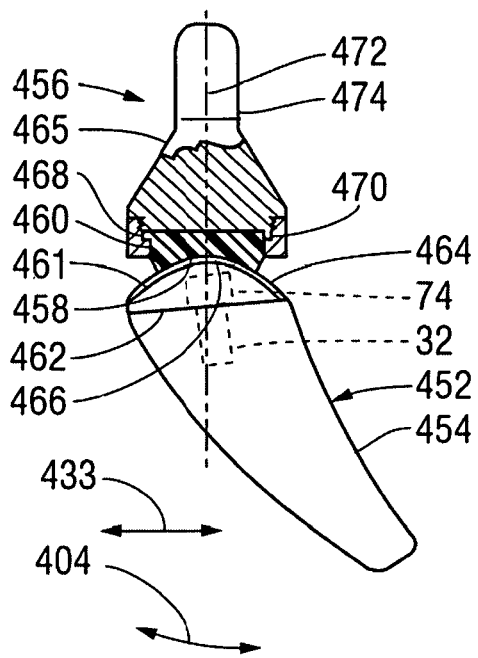
FIG. 27 is a partly sectional medial view of an ankle replacement prosthesis built in accordance with a third version of the second embodiment of the invention.
Figure 28:
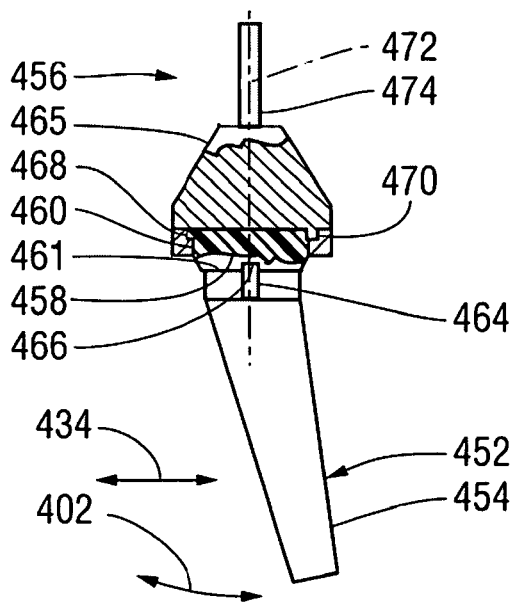
FIG. 28 is a partially sectional posterior view of the prosthesis of FIG. 27.

FIGS. 27 and 28 show an ankle replacement prosthesis 450 built in accordance with a third version of the second embodiment of the invention, again to prevent inversion/eversion rotation, in the directions of arrow 402. FIG. 27 is a partly sectional medial view of the prosthesis 450 while FIG. 28 is a partly sectional posterior view thereof. Again, the ankle replacement prosthesis 450 includes a talocalcaneal component 452 having a stem 454 that extends to the weight bearing portion 246 of the calcaneus 229 within the talocalcaneal compound 229 (all as shown in FIG. 14). The ankle replacement prosthesis 450 additionally includes a tibial component 456. A tibial contact surface 458 of a socket 460 within the tibial component 456 and a talocalcaneal contact surface 461, extending along a head 462 of the talocalcaneal component 452 are each rounded in the anterior/posterior directions of arrow 433, and are each straight in the medial/lateral directions of arrow 434, permitting relative rotation in the dorsal/plantar directions of arrow 404, while preventing inversion/eversion rotation, in the directions of arrow 402. Relative movement in the medial/lateral directions of arrow 434 is prevented by contact between a rib 464 extending along the talocalcaneal contact surface 461 and a groove 466 extending along the tibial contact surface 458. Other aspects of the ankle replacement prosthesis 400 are as described above regarding the ankle replacement prosthesis 12. Preferably, the socket 460 is pivotally attached to a housing 465 within the tibial component 456 by a number of outwardly extending tabs 468 spaced apart from a number of inwardly-extending tabs 470, allowing limited axial rotation of the talocalcaneal component 452 around an axis 472.

Preferably, each of the ankle replacement prostheses 400, 420, 450 is provided with a neck 32 engaging a neck receiving hole 74, within the head 412, 432, 460, as described above in reference to FIGS. 20-22 allowing adjustments as described above. Since the tibial components 409, 426, 456 of these ankle replacement prostheses 400, 420, 450 have features that need to be aligned with the directions of arrows 402 to prevent inversion/eversion rotation, each of these tibial components 409, 426, 456 is preferably provided with a stem 474 that is flattened or otherwise non-circular, to be inserted against a mating bone surface prepared using a rasp.

While the invention has been described in terms of preferred embodiments with some degree of particularity, it is understood that this description has been given only by way of example, and that many changes can be made without departing from the spirit and scope of the invention, as defined in the appended claims.

What is claimed is:

1. A method for replacing an ankle within a foot, comprising:
   a) attaching a tibial component of an ankle replacement prosthesis having a tibial contact surface to a distal end of a tibia;
   b) forming a talocalcaneal compound by fusing a talus to a calcaneus within the foot;
   c) forming a slot within the talocalcaneal compound, following step b), extending from a proximal surface of the talus through the talus and through the calcaneus into a lower posterior portion of the calcaneus;
   d) attaching a talocalcaneal component of the ankle replacement prosthesis, having a talocalcaneal contact surface configured to move in contact with the tibial contact surface, to the talocalcaneal compound with a stem of the talocalcaneal component extending through the slot formed in step c) within the talocalcaneal compound from the proximal surface of the talus through the talus and through the calcaneus into a lower posterior portion of the calcaneus.

2. The method of claim 1, wherein the talus is fused to the calcaneus in step b) by fusing the subtalar joint using a screw extending within the talus and the calcaneus.

3. The method of claim 1, additionally comprising, before steps a) and b), exposing a proximal surface of the talus and a distal end of the tibia through an anteriolateral longitudinal incision starting about 10 cm above the ankle extending distally over the neck of the talus and being directed laterally and distally to end just below the lateral malleolus, with. neurovascular structures and anterior tendons being retracted medially after longitudinal incision of the superior and inferior ankle retinaculum.

4. The method of claim 1, additionally comprising, before steps a) and b), performing an osteotomy of the distal fibula with a distal portion of the fibula remaining attached to ligaments within the foot while the tibia is rotated in a posterior direction away from the foot.

5. The method of claim 4, additionally comprising, after step d),
   repairing the fibular osteotomy temporarily by clamping the osteotomy surfaces together;
   testing the ankle replacement prosthesis for function, position, and stability;

making an adjustment to the ankle replacement prosthesis; and repairing the fibular osteotomy permanently by fastening the osteotomy surfaces together with a plate and screws.

6. The method of claim 5, wherein the adjustment to the ankle replacement prosthesis is made with a trail version of the ankle replacement prosthesis, and the method additionally comprises replacing the trial version of the ankle replacement prosthesis with a permanent version of the ankle replacement prosthesis before repairing the fibular osteotomy permanently.

7. The method of claim 6, wherein the adjustment to the ankle replacement prosthesis includes rotating a head, including the talocalcaneal contact surfaces and a neck receiving hole attached to a neck within the talocalcaneal component, on the neck.

8. The method of claim 7, wherein the neck receiving hole is eccentrically disposed relative to the talocalcaneal contact surfaces.

9. The method of claim 8, wherein the adjustment to the ankle replacement prosthesis includes replacing the head within the talocalcaneal component with another head having a different level of eccentricity.

10. The method of claim 5, wherein the adjustment to the ankle replacement prosthesis includes replacing a head, including the talocalcaneal contact surface and a neck receiving hole attached to a neck within the talocalcaneal component, extending to a first depth within the head, with another head having a neck receiving hole configured to engage the neck at a second depth within the head, significantly different from the first depth.

11. The method of claim 1, wherein step c) is preceded by removing a predetermined thickness of bone from a crown of the talus to form a talar plafond.

12. The method of claim 11, wherein the predetermined thickness of bone is removed from the crown of the talus by a method comprising:

clamping the foot within a foot holding fixture to be held with surfaces of a sole of the foot against a main plate;

moving a guide plate disposed parallel to the main plate toward the main plate until a talus contacting surface, attached to the guide plate and spaced away from the guide plate through a first distance, contacts the crown of the talus;

removing the talus contacting surface from the guide plate; and removing bone having a thickness equal to the first distance from the crown of the talus using a saw moving along the guide plate.

13. The method of claim 11, wherein step c) is additionally preceded by a method comprising:

attaching a paddle guide extending adjacent the talar plafond to bones within the foot; and tracing an edge of a slot within the paddle guide to form a marking on the talar plafond indicating a location and angle for forming the slot within the talocalcaneal compound.

14. The method of claim 1, wherein step a) is preceded by forming a conical cavity extending within a distal portion of the tibia in a proximal direction from a distal end of the tibia for accepting a conical hub portion of the tibial end of the ankle replacement prosthesis.

15. The method of claim 1, wherein step a) is additionally preceded by removing a predetermined thickness of bone from an inferior articular surface of the tibia to form a tibial plafond.

16. The method of claim 15, wherein the predetermined thickness of bone is removed from the inferior articular surface of the talus by a method comprising:

fastening a tibial guide to the tibia with a contact surface of the tibial guide in contact with the inferior articular surface of the tibia; and removing bone having a thickness equal to a second distance from the interior articular surface of the tibia using a saw operating within a slot within the tibial guide spaced away from the contact surface in the tibial guide by a distance equal to the second distance.

\* \* \* \* \*